United States Patent
Hayes et al.

(12)

(10) Patent No.: US 6,744,024 B1
(45) Date of Patent: Jun. 1, 2004

(54) REACTION AND TEMPERATURE CONTROL FOR HIGH POWER MICROWAVE-ASSISTED CHEMISTRY TECHNIQUES

(75) Inventors: Brittany L. Hayes, Charlotte, NC (US); Michael J. Collins, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 111 days.

(21) Appl. No.: 10/064,261

(22) Filed: Jun. 26, 2002

(51) Int. Cl.⁷ .............................................. H05B 6/64
(52) U.S. Cl. ..................... 219/679; 219/686; 219/746
(58) Field of Search ............................. 219/679, 686, 219/704, 705, 707, 710, 711, 718, 715, 716, 695, 696, 691–693, 745, 746, 748, 756; 333/248, 212, 227; 204/157.43; 422/21, 87.12, 87.13, 103

(56) References Cited

U.S. PATENT DOCUMENTS

| | | | |
|---|---|---|---|
| 4,180,918 A | * | 1/1980 | Ostrowski .................... 34/393 |
| 4,835,354 A | | 5/1989 | Collins et al. |
| 5,215,715 A | | 6/1993 | Haswell et al. |
| 5,238,710 A | | 8/1993 | Ahmad et al. |
| 5,387,397 A | | 2/1995 | Strauss et al. |
| 5,393,492 A | | 2/1995 | Di Martino et al. |
| 5,420,039 A | | 5/1995 | Renoe et al. |
| 5,830,417 A | | 11/1998 | Kingston |
| 5,883,349 A | | 3/1999 | Kingston |
| 5,932,075 A | | 8/1999 | Strauss et al. |
| 6,011,247 A | | 1/2000 | Grillo et al. |
| 6,054,695 A | | 4/2000 | Lautenschlager |
| 6,120,741 A | | 9/2000 | Jacquault et al. |
| 6,136,157 A | | 10/2000 | Lindeberg et al. |
| 6,288,379 B1 | | 9/2001 | Greene et al. |
| 6,368,994 B1 | | 4/2002 | Sklyarevich |
| 6,630,652 B2 | * | 10/2003 | Jennings ..................... 219/679 |

FOREIGN PATENT DOCUMENTS

| | | |
|---|---|---|
| DE | 43 25 667 A1 | 2/1995 |
| EP | 0 467 625 A | 1/1992 |
| JP | 02-090983 | 3/1990 |
| JP | 06-096856 | 4/1994 |
| JP | 08-136422 | 5/1996 |
| WO | WO 95/15671 A1 | 6/1995 |

OTHER PUBLICATIONS

I. Plaxl et al.; Hydrolysis of sucrose by conventional and microwave heating in stirred tank reactor, The Chemical Engineering Journal 59 (1995): pp. 253–257; Elsevier Science S.A.

Gunn Oscillators; www.millimeterwave.com/oscillators.html; 1 page, ZAX Millimeter Wave Corporation, San Dimas, CA.

John Stephens; Peltier CPU Cooling; PCMECHANIC; www.pcmech.com/show/processors/140/; Last Updated Mar. 30, 2001; 2 pages.

Michael J. Collins, PH.D.; *Drug Discovery at the Speed of Light*; Presented at the Drug Discovery Technology, Boston, MA; Aug. 14, 2001; pp. 1–8.

* cited by examiner

*Primary Examiner*—Tu Ba Hoang
(74) *Attorney, Agent, or Firm*—Summa & Allan, P.A.

(57) ABSTRACT

A method is disclosed for carrying out microwave assisted chemical reactions. The method includes the steps of placing reactants in a microwave-transparent vessel, placing the vessel and its contents into a microwave cavity, applying microwave radiation within the cavity and to the vessel and its contents while concurrently externally cooling the vessel conductively.

52 Claims, 16 Drawing Sheets

Negishi Reaction 2-chloropyridine 2-methylphenyl zinc iodide bis(tri-*t*-butylphosphine) palladium(0)

2-o-tolylpyridine

Diels-Alder Reaction furan | diethylacetylene dicarboxylate | 1,2-dicarboxylic acid diethyl ester-3,6-epoxycyclohexa-1,4-diene

REACTION AND TEMPERATURE CONTROL FOR HIGH POWER MICROWAVE-ASSISTED CHEMISTRY TECHNIQUES

CROSS REFERENCE TO RELATED APPLICATIONS

The present invention is related to copending and commonly assigned applications Serial Nos. 10/063,914 filed May 23, 2002; 10/063,628 filed May 3, 2002; 10/126,838 filed Apr. 19, 2002; and 09/773,846 filed Jan. 31, 2001. These applications are incorporated entirely herein by reference.

BACKGROUND OF INVENTION

The present invention relates generally to the field of microwave-assisted chemistry techniques, and in particular relates to more sophisticated techniques such as chemical synthesis carried out on relatively small volumes of reactants.

Microwave-assisted chemistry techniques are generally well established in the academic and commercial arenas. Microwaves have some significant advantages in heating certain substances. In particular, when microwaves interact with substances with which they can couple, most typically polar molecules or ionic species, the microwaves can immediately create a large amount of kinetic energy in such species which provides sufficient energy to initiate or accelerate various chemical reactions. Microwaves also have an advantage over conduction heating in that the surroundings do not need to be heated because the microwaves can react instantaneously with the desired species.

The term "microwaves" refers to that portion of the electromagnetic spectrum between about 300 and 300,000 megahertz (MHz) with wavelengths of between about one millimeter (1 mm) and one meter (1 m). These are, of course, arbitrary boundaries, but help quantify microwaves as falling below the frequencies of infrared radiation but above those referred to as radio frequencies. Similarly, given the well-established inverse relationship between frequency and wavelength, microwaves have longer wavelengths than infrared radiation, but shorter than radio frequency wavelengths.

Because of their wavelength and energy, microwaves have been historically most useful in driving reactions in relatively large sample amounts. Stated differently, the wavelengths of most microwaves tend to create multi-mode situations in cavities in which the microwaves are being applied. In a number of types of chemical reactions, this offers little or no disadvantage, and microwave techniques are commercially well established for reactions such as digestion or loss-on-drying moisture content analysis.

Microwaves, however, have been less successfully applied to small samples of materials. Although some chemistry techniques have the obvious goal of scaling up a chemical reaction, in many laboratory and research techniques, it is often necessary or advantageous to carry out chemical reactions on small samples. For example, the availability of some compounds, may be limited to small samples. In other cases, the cost of reactants may discourage large sample sizes. Other techniques, such as combinatorial chemistry, use large numbers of small samples to rapidly gather a significant amount of information, and then tailor the results to provide the desired answers, such as preferred candidates for pharmaceutical compounds or their useful precursors.

Microwave devices with larger, multimode cavities that are suitable for other types of microwave-assisted techniques (e.g. drying, digestion, etc.) are generally less-suitable for smaller organic samples because the power density in the cavity is relatively low and non-uniform in its pattern.

Accordingly, the need for more focused approaches to microwave-assisted chemistry has led to improvements of devices for this purpose. For example, in the copending and commonly assigned (CEM Corporation, 3100 Smith Farm Road, Matthews, N.C. 28106) U.S. applications referred to above, and the commercially available devices sold under the assignee's DISCOVER™ trademark, the assignee of the present invention has provided a single mode focused microwave device that is suitable for small samples and for sophisticated reactions such as chemical synthesis. Single mode devices are also available from Personal Chemistry Inc., Boston, Mass., under the EMRYS™ trademark.

The very success of such single mode devices has, however, created associated problems. In particular, the improvement in power density provided by single-mode devices can cause significant heating in small samples, including undesired over-heating in some circumstances.

Accordingly, some potential advantages remain to be accomplished. For example, in chemical synthesis the temperature at which a particular reaction is initiated, run or maintained can be critical to the reaction's success. At various temperatures, products or reactants can degrade undesirably or competing reactions can form compounds other than those desired or intended. Because single mode instruments can be so efficient in heating certain materials, this efficiency can occasionally result in overheating of synthesis reactants and thus negate the advantage provided by the single mode instruments. Stated differently, the application of microwaves controls the efficiency of the reaction rather than the bulk temperature of the reactants (and potentially the solvent, if used). Thus, greater efficiency is gained when a greater amount of microwave energy can be applied without producing an undesired increase in the bulk temperature of the materials being irradiated. Thus, although bulk temperature is a factor to be controlled, it represents a by-product of the successful use of microwaves rather than a requirement.

Furthermore, most microwave temperature control is often accomplished using the duty cycle (the ratio of the duration (time) that a signal is on to the total period of the signal) of the microwave device; i.e., turning the applied power off and on again on a repeated basis. Thus, in many cases, when a microwave device is set to run at "50% power", the applied power (usually expressed in watts, W) remains the same, and the ratio of the duty cycle is reduced; i.e., the "on" portion of the cycle is decreased and the "off" portion is increased. Although such macro control is suitable for larger samples or less sensitive chemical procedures such as digestion and moisture analysis, it can be quite unsatisfactory for carrying out sophisticated chemical reactions or for using the small samples that are typical for laboratory-scale organic synthesis techniques.

The duty cycle technique for moderating power, and thus secondarily temperature, also has the disadvantage of being somewhat inefficient. Stated differently, when the duty cycle is moderated, molecules are being intermittently, rather than continuously, excited by microwave radiation. Thus, instead of being maintained at a particular energy level or exposed to a continuous power level, the molecules are continually cycling between a microwave-excited and a normal or ground state. As a result, the advantages of using microwaves to apply energy to molecules for the purpose of initiating or accelerating sophisticated reactions can be compromised.

An extended discussion of the nature and situational disadvantages of the duty cycle in microwave assisted chemistry is set forth in commonly assigned U.S. Pat. No. 6,288,379, the contents of which are incorporated entirely herein by reference. In particular, a useful background discussion is set forth at column 1 line 66 through column 2 line 52.

Thus, although the duty cycle technique has it disadvantages and inefficiencies, it has historically been the only method available to prevent reactions of any type, and particularly sophisticated organic synthesis reactions, from proceeding above a desired temperature.

Accordingly, the needs exists for a microwave technique that can apply greater amounts of microwave energy without generating the high bulk temperatures that can be undesirable or even fatal to certain reactions and without sacrificing the advantages of the interaction of the microwaves with the reactants.

Therefore, it is ,an object of the invention to provide a microwave technique that can remain sensitive enough to control the temperature of sophisticated organic synthesis reactions, but without sacrificing the advantages of the interaction of the microwaves with the reactants as often as possible.

SUMMARY OF INVENTION

The invention meets this object with a method of carrying out microwave assisted chemical reactions in which the method comprises placing reactants in a microwave-transparent vessel, placing the vessel and its contents into a microwave cavity; and applying a continuous single mode of microwave radiation within the cavity and to the vessel and its contents while concurrently externally cooling the vessel.

In another aspect, the invention is a method of carrying out microwave assisted chemical reactions, comprising placing reactants in a microwave-transparent pressure resistant vessel and sealing the vessel, placing the sealed vessel and its contents into a microwave cavity, applying microwave radiation continuously within the cavity and to the vessel and its contents while monitoring the temperature of the vessel or its contents, and while concurrently externally cooling the sealed vessel and its contents.

In yet another aspect, the invention is a method of carrying out microwave assisted chemical reactions comprising placing reactants in a microwave-transparent vessel, placing the vessel and its contents into a microwave cavity, monitoring the temperature of the vessel or its contents, applying a continuous single mode of microwave radiation within the cavity and to the vessel and its contents until the temperature reaches a desired setpoint, and concurrently externally cooling the vessel and its contents while applying the continuous microwave radiation to maintain the temperature substantially at the setpoint.

In a further aspect, the invention is a method of carrying out chemical reactions at specific temperatures comprising applying energy to reactants in a vessel using a source other than conduction heating of the vessel or the reactants, while concurrently cooling the vessel by conduction by contacting the exterior of the vessel with a fluid.

In another aspect, the invention is a method of carrying out chemical reactions comprising applying energy to reactants in a vessel in an instrument that uses a source other than conduction heating of the vessel or the reactants to heat the reactants, concurrently cooling the vessel in the instrument by providing a flow of conduction fluid against the vessel in the instrument, concurrently monitoring the temperature of the vessel or its contents in the instrument, and adjusting the heating source to maintain the desired temperature at the cooling capacity that the instrument can provide to the, vessel.

In yet another aspect, the invention is an instrument for carrying out microwave assisted chemical reactions. In this aspect, the invention includes a microwave cavity, a microwave-transparent vessel in the cavity, a detector for monitoring the temperature of the vessel or its contents in the cavity, means for applying a continuous single mode of microwave radiation within the cavity and to the vessel and its contents until the temperature reaches a desired setpoint as measured by the detector, means for concurrently externally cooling the vessel and its contents while applying the continuous microwave radiation, and means for maintaining the temperature substantially at the setpoint while applying the microwave radiation.

The foregoing and other objects and advantages of the invention and the manner in which the same are accomplished will become clearer based on the followed detailed description taken in conjunction with the accompanying drawings in which:

DETAILED DESCRIPTION

Figure 1:
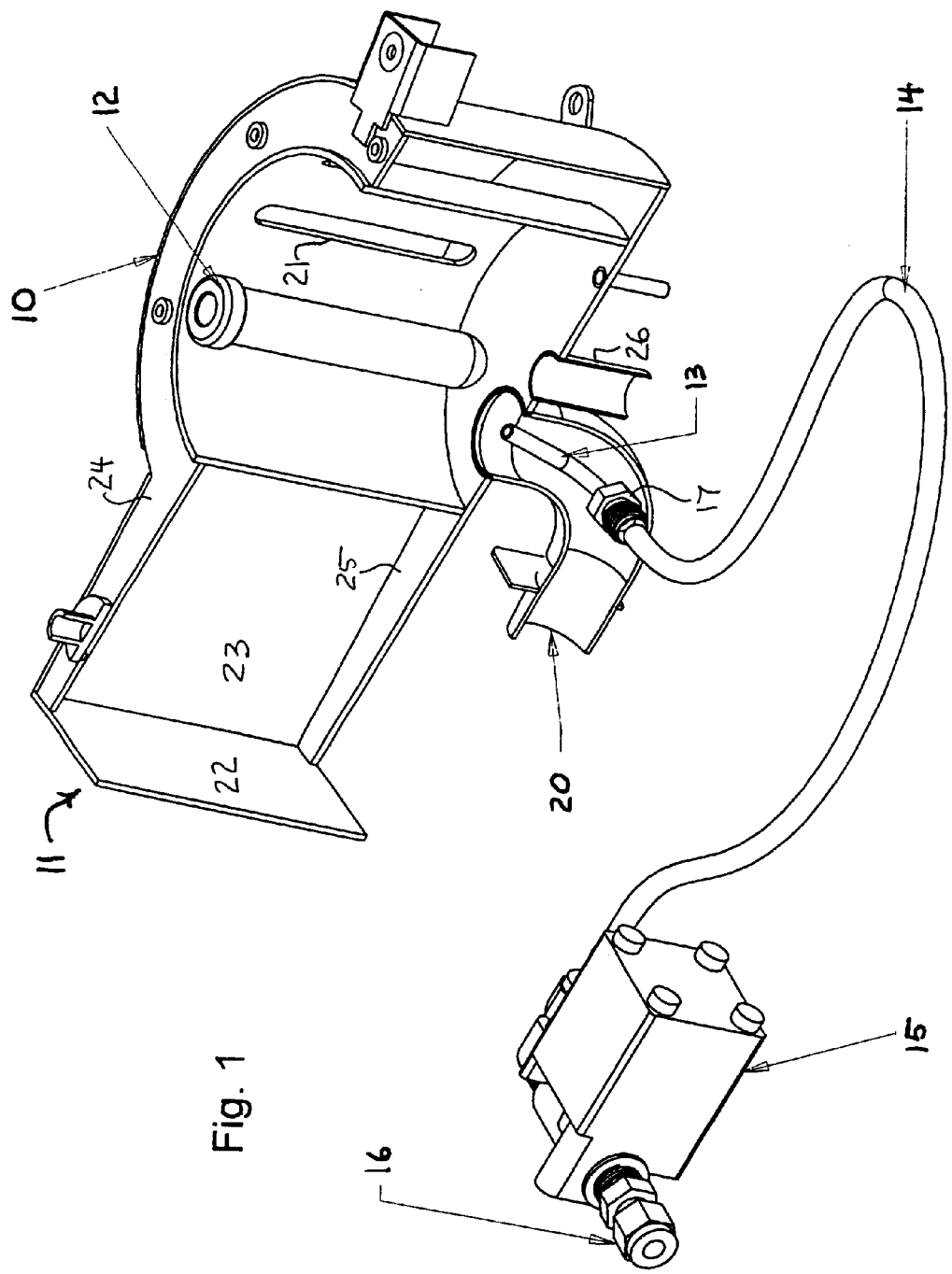
FIG. 1 is a perspective view of portions of the instrument of the present invention.

In its broadest aspect, the present invention is a method of carrying out chemical reactions, particularly sophisticated or sensitive chemical reactions at specific temperatures, by applying energy to reactants or reactants in a vessel using a source other than conduction heating while concurrently cooling the vessel by conduction by contacting the exterior of the vessel with a fluid. The net result is to maintain a desired temperature while still having capability of applying significant amounts of energy other than by heat conduction.

In a strict sense, the term "reagent" refers to "a substance used in a reaction for the purpose of detecting, measuring, examining, or analyzing other substances," Lexis, Hawley's Condensed Chemical Dictionary, 12$^{th}$ Ed. (1993), Van Nostrand Reinhold Company; while the term "reactant" refers to, "a substance that reacts with another one to produce a new set of substances (products)," McGraw-Hill Access Science (www.accessscience.com). Although these terms are frequently used interchangeably, they will be used properly herein.

In preferred embodiments, the step of applying energy comprises exposing the vessel and the reactants—and not necessarily the solvents—to electromagnetic radiation, which in turn is selected from the group consisting of microwaves, infrared radiation, radiation in the visible portion of the spectrum, and ultraviolet radiation, with microwaves being most preferred. The nature and frequencies of each of these sets of electromagnetic radiation are well understood and will not be otherwise discussed in detail herein.

In this aspect, the method can further comprise directing a flow of air from the instrument to the vessel to provide the flow of conduction fluid. As discussed elsewhere herein, the flow of air can be from a fan, from a source of compressed air, from a regulator, or from any other appropriate source that does not otherwise interfere with the heating or the reaction itself.

Although the term "vessel" is used herein, it will be understood that the invention is not limited to sealed or unsealed vessels of any particular size or shape. Additionally, the term vessel can include other physical arrangements for handling the reactants, including flow-through systems.

In more preferred embodiments, the method additionally comprises concurrently monitoring the temperature of the vessel or its contents in the instrument, and adjusting the heating source to maintain the desired temperature at the cooling capacity that the instrument can provide to the vessel. The temperature is preferably monitored using a device or method that does not interfere with the concurrent heating and cooling steps. Thus, in preferred embodiments, temperature measurement is often carried out optically, most preferably by using an infrared (IR) temperature sensor. An IR sensor is particularly useful when the frequencies being applied to supply energy to the reactants are other than IR, because the infrared sensor measures radiation emitted by the vessel or its contents and does not need to be in direct contact with the vessel. Accordingly, it can be positioned in a spot that does not cause interference with electromagnetic radiation and does not interfere with the cooling flow of fluid, usually air.

Thus, temperature control can be carried out by varying the cooling while applying the microwave radiation in a constant manner, or by varying the application of microwaves while providing a constant cooling flow.

In another aspect, the method comprises placing reactants in a microwave-transparent vessel, potentially but not necessarily including placing the reactants in pressure-resistant vessels which can be sealed prior to the application of microwave radiation. The vessel and its contents are then placed into a microwave cavity and a continuous single mode of microwave radiation is applied within the cavity to the vessel and its contents while concurrently externally cooling the vessel.

Because of the nature of microwaves, which follow well understood laws of wave propagation, the production of a single mode is most often accomplished by designing a cavity having a geometry that supports a single mode. As used herein and as generally well-understood in this field, the term "mode" refers to the permitted electromagnetic field pattern within a cavity.

Microwave modes are generally referred to by the $TE_{n,l,m}$ designation (TM for the magnetic field) where the subscripts refer to the number of nulls in the propagated direction. Cavities that can support single modes are set forth in the art and are generally understood by those familiar with microwaves and their propagations. An exemplary cavity for propagating a single mode of microwave radiation is set forth in the previously incorporated applications. The invention is not, however, limited to single mode techniques or cavities.

The application of a continuous microwave radiation is preferably accomplished using a resonant inverter switching power supply as set forth in previously incorporated U.S. Pat. No. 6,288,379. Thus, the term "continuous" is used herein in a descriptive rather than an absolute sense and refers to applying radiation from a source while driving the source at a frequency greater than 60 hertz. More preferably, the source is driven at a frequency greater than 600 hertz, even more preferably at greater than 6,000 hertz and most preferably at frequencies between about 10,000 and 250,000 hertz. As described in the '379 patent, this permits the power to be applied at a more even level over a longer period of time than in conventional devices which operate on 50 cycle (typical in Europe) or 60 cycle alternating current (standard in the United States). Any appropriate microwave source can be used that is consistent with the other aspects of the invention and typically comprises a magnetron, a klystron, or a solid state source, such as a Gunn diode.

The method can also include the step of using various robotic transfers to both place the reactants in a microwave transparent vessel and to place the vessel and contents into a microwave cavity.

Because one of the goals of the invention is to provide careful control of reaction temperature, the step of cooling the vessel and its contents generally comprises directing an airflow over (around) the vessel at a rate (typically measured as volume per unit time or a given pressure) sufficient to maintain the vessel and its contents at a desired temperature. For typical organic reactions that are taking place in the range of between about 40° C. and 250° C., an airflow directed or generated at between about 1 and 80 pounds per square inch (psi) has been found to be appropriate. From a functional standpoint, the airflow is sufficient to provide cooling while less than that which would cause undesired or unnecessary buffeting or other mechanical problems, or that would lower the bulk temperature below a point that was desired for a particular reaction scheme or other purpose.

The method can also comprise varying the rate and degree of cooling, for example by changing the rate of airflow in response to the measured temperature, a step which is preferably carried out while the microwaves are being applied and the vessel is being externally cooled.

In another aspect, the method comprises placing reactants in a microwave transparent vessel, placing the vessel and its contents into a microwave cavity, continuously monitoring the temperature of the vessel or its contents, and applying a continuous single mode of microwave radiation within the cavity and to the vessel and its contents until the temperature reaches a desired set point, and then concurrently externally cooling the vessel and its contents while applying the continuous microwave radiation to maintain the temperature substantially at the set point. Most preferably, the cooling step comprises cooling the vessel with a fluid from a fluid source and the step of applying the microwave radiation comprises maximizing the microwave power at the capacity of the cooling source while maintaining the temperature substantially at the set point.

Stated differently, the goal is to apply as much microwave power (energy) to the reactants as possible while avoiding exceeding a desired set point temperature. Given that the capacity of the cooling system will be a determining factor in how much heat can be transferred away from the vessel and the reactants, the microwave power is maintained as high as possible, consistent with the cooling capacity of the cooling device associated with the microwave instrument.

Because chemical reactions can be carried out in stages, often desirably so, the method can further comprise changing the set point at a desired time or stage of the reaction and then again carrying out the steps of applying microwave radiation and external cooling to reach and maintain the temperature at the new set point.

Thus, for reactants (as opposed to solvents) the method of the present invention provides an enhanced reaction rate at any given temperature as compared to a thermally or conductively heated reaction. This results from the direct molecular heating provided by microwave radiation, which in turn can produce superheated molecules. Some of that energy will, of course, transfer to the solution and create the bulk temperature that is measured. Because of the cooling step, the invention offers similar advantages over more conventional microwave techniques that aggressively decrease the applied power in order to control the bulk temperature.

Stated differently, a reaction carried out at 150° C. that is initiated and maintained by conductive heating will proceed at a given rate. If the temperature of the same reaction is maintained at 150° C. using microwave heating, the rate will be enhanced because of the direct molecular heating. Even better, however, using the invention, a reaction carried out at 150° C. using microwave radiation and proactive cooling will have the highest rate because it provides the greatest opportunity to maximize the microwave energy being applied directly to the reactants.

As known to those familiar with microwave radiation and microwave-assisted chemistry, in the microwave frequency ranges, the polar (or ionic) molecules will try to constantly align with a rapidly changing electric field. This movement creates the bulk heat. The resulting bulk temperature can be disadvantageous when heat sensitive reactions are carried out, or reactions using heat sensitive reactants or that create heat sensitive products. Proteins are an example of molecules that tend to be overly sensitive to high temperatures, and thus hard to heat moderately using microwaves, absent the cooling step of the invention.

The method of the invention is particularly useful with cross-coupling reactions that produce carbon-carbon bonds in complex organic syntheses such as the development of pharmaceutical products. These include the Heck, Kharash, Negishi, Stille, or Suzuki reactions which are well known in the art. In general, diaryl compounds are synthesized by a number of catalytic cross-coupling reactions from arylhalides or triflates and arylmetal reagents; for example, Grignard reagent (Kharasch reaction), arylzinc reagent (Negishi reaction), palladium-catalyzed vinylic substitution (Heck reaction), aryltin reagent (Stille reaction), arylboron reagent (Suzuki reaction), arylsilyl reagent, etc.

For example, in the Negishi reaction an aryl chloride is reacted with an aryl zinc halide. The reaction is palladium catalyzed in tetrahydrofuran. Two competing reactions can occur. In the undesired competing reaction, the aryl zinc halide simply substitutes with itself to provide a biaryl molecule. Instead, the preferred reaction is to produce a substituted biaryl compound with zinc dihalide as the byproduct. In comparative tests, and using the method of the invention, the desired reaction that produced the disubstituted aromatic compound had a much higher yield than when the reaction was carried out without the cooling step. This results, of course, from control of the temperature to prevent the competing reaction from progressing.

Stated differently, the invention can drive a microwave activated reaction complex, rather than a thermally-driven activated competing reaction, to produce a desired reaction in a manner that would be difficult using conventional conduction heating.

Similar advantages are expected for Diels-Alder reactions (i.e., the reaction of . unsaturated carbonyl compounds with conjugated dienes).

The drawings illustrate a preferred instrument suitable for carrying out the method steps of the present invention.

FIG. 1 is a perspective view of a presently preferred embodiment of carrying out the method of the present invention. FIG. 1 illustrates a microwave cavity broadly designated at 10, which is of the same type as the cavity described and claimed in copending and previously incorporated "914; "628; "838; and "846 applications. Because the nature of the cavity and the operation of the entire instrument is clearly set forth in these applications, the cavity will not be described in detail herein other than to explain the invention. FIG. 1 also shows a portion of the waveguide 11 into which a microwave source propagates microwaves for transmission into the cavity 10.

A reaction vessel 12 is positioned in the cavity 10 in a manner described in the incorporated applications. Thus, it will be understood that although FIG. 1 shows the reaction vessel 12 as being suspended without evident support, in reality it is maintained in place by the additional structure (preferably an attenuator) described in those applications.

In the preferred embodiment, the cooling step is carried out by directing a flow of cooling fluid, preferably air, from the cooling nozzle 13 over and around the vessel 12. In turn, the cooling fluid reaches the cooling nozzle through the illustrated tubing 14, the flow of which is controlled by the solenoid 15. As set forth with respect to the method aspects of the invention, appropriate software can be used to control the solenoid and in turn, the flow of fluid through the tubing 14 to adjust the amount of cooling flow of fluid from the cooling nozzle 13 into the cavity 10 and against the reaction vial 12. The nature and operation of all of these elements is well understood in this and other arts, and need not be discussed in detail herein other than to describe the invention.

Some additional elements illustrated in FIG. 1 include an inlet fitting 16 for connecting the solenoid 15 and the tubing 14 to a source of cooling fluid whether compressed air, or some other gas. The tubing 14 is connected to the cooling nozzle 13 through the fitting 17 and in preferred embodiments the cooling nozzle is placed within an exhaust housing 20 beneath the cavity 10. FIG. 1 also illustrates that in the preferred embodiment, which is a version of the DISCOVER™ tool referred to earlier herein, the microwave cavity 10 has circular or cylindrically shaped portions, and includes a plurality of slots 21 through which microwaves propagate as they enter from the waveguide 11. In the illustrated embodiment, the waveguide 11 is generally rectangular in shape and is formed of several perpendicularly arranged walls of which the largest illustrated in FIG. 1 are the walls 22 and 23. Portions of the top wall 24 and a bottom wall 25 are also illustrated in FIG. 1. A cylindrical housing 26 adjacent the bottom of the cavity 10 is described in more detail in the incorporated applications, but generally serves as a housing for a temperature-sensing device such as an infrared temperature-measuring device.

Figure 2:
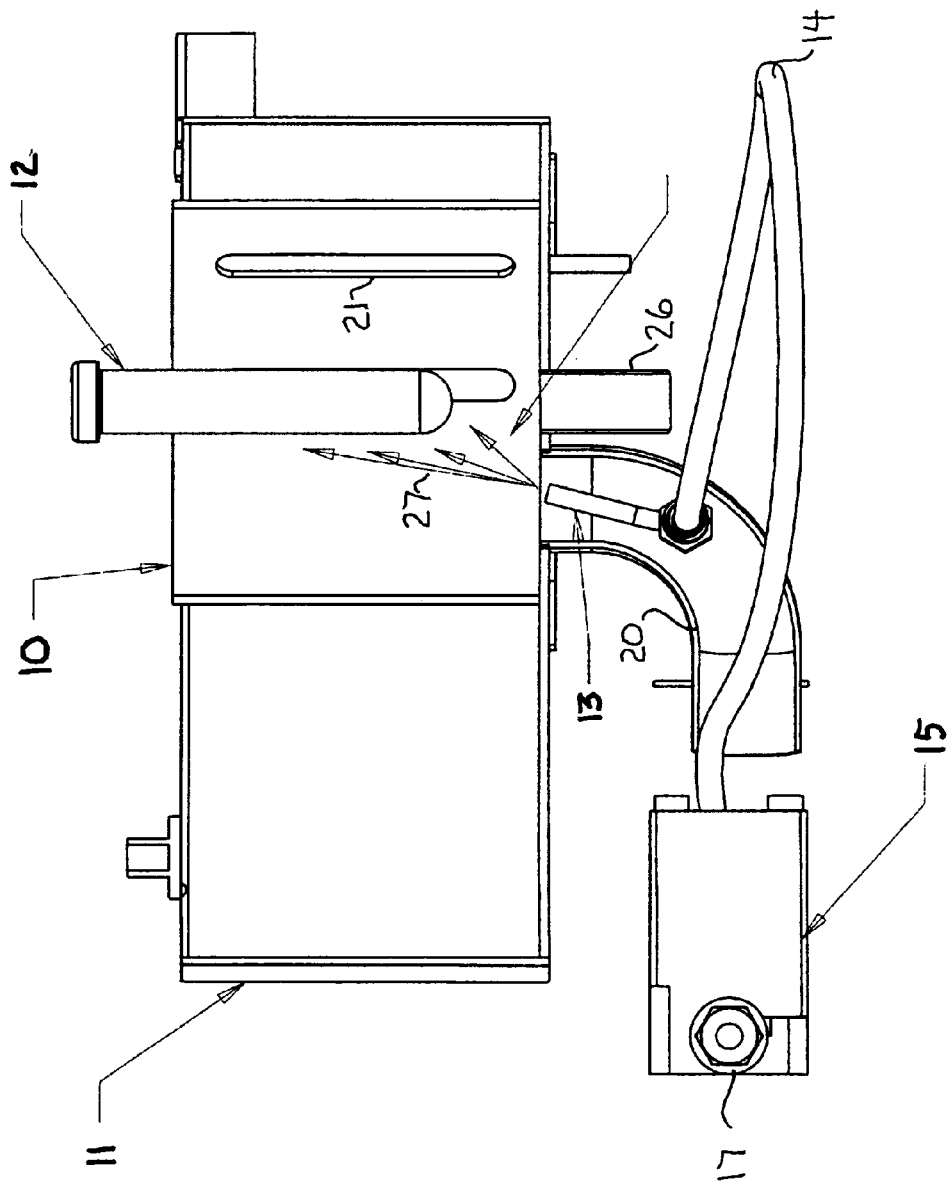
FIG. 2 is a cross-sectional view of the elements illustrated in FIG. 1.

FIG. 2 is a cross-sectional view of the same portion of the preferred instrument as illustrated in FIG. 1. All of the elements are the same and maintain the same reference numerals. FIG. 2, however, also includes the arrows 27 that help illustrate the direction of flow of the cooling fluid.

In another aspect the invention is an instrument for carrying out the microwave assisted chemical reactions according to the method of the invention. In this aspect, the invention comprises a microwave cavity, a microwave transparent vessel in the cavity, a detector for monitoring the temperature of the vessel or its contents in the cavity, means for applying a continuous single mode of microwave radiation within the cavity and to the vessel and its contents until the temperature reaches a desired set point as measured by the detector, means for concurrently externally cooling the vessel and its contents while applying the continuous microwave radiation, and means for maintaining the temperature substantially at the set point while applying the microwave radiation.

Figure 3:
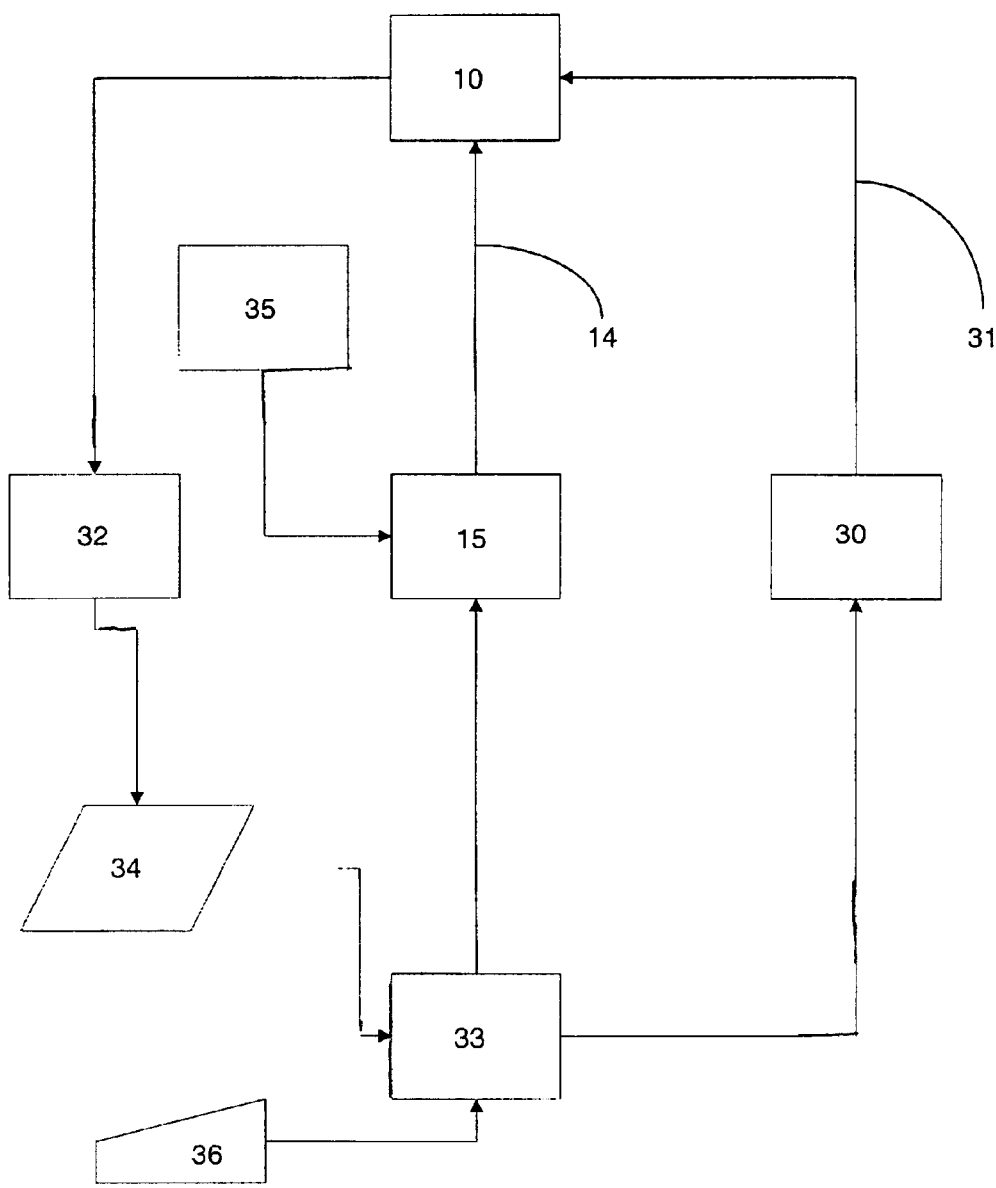
FIG. 3 is a schematic diagram of the elements of the instrument of the invention.

FIG. 3 schematically illustrates some of these elements and compliments the illustration of FIGS. 1 and 2. FIG. 3 illustrates the cavity, again designated at 10, into which the reaction vessel 12 (FIG. 1) can be placed. A source 30 of microwave radiation is in communication with the cavity 10 as designated by the arrow 31. This path of communication generally includes the waveguide 11, portions of which are illustrated FIGS. 1 and 2. The temperature detector is designated at 32 and in preferred embodiments comprises an infrared temperature detector as described in the incorporated applications. As set forth therein, an infrared detector is particularly useful because it detects frequencies different than those being applied from the source 30 into the cavity 10. Additionally, an infrared detector does not require actual physical contact with the item for which the temperature is being measured. Appropriate infrared temperature detectors are commercially available, well understood, and quite durable and thus meet a number of requirements for this use.

FIG. 3 also illustrates that in preferred embodiments the instrument comprises a processor 33 that is in signal communication (i.e., electrical communication) with the detector 32. FIG. 3 illustrates this using the data symbol 34 to illustrate the flow of temperature information from the detector 32 to the processor 33. The term "processor" as used herein refers to devices that can store instructions and execute them. In preferred embodiments the processor is a semiconductor microprocessor, the nature and operation of which are widely understood in this and other arts. Such processors are also referred to as "CPU's" (central processing unit). The processor preferably is in communication with an input device (most typically a keyboard or keypad) for providing the processor with data selected from the group consisting of microwave power levels, durations of microwave application and setpoint temperatures.

As described with respect to FIGS. 1 and 2, the means for cooling the vessel 12 and its contents preferably comprises a source of cooling fluid and a fluid communication path from the source to the cavity 10. As illustrated in FIGS. 1 and 2, and schematically in FIG. 3, the fluid communication path includes the tubing 14 illustrated in FIG. 1 and schematically represented in FIG. 3 along with the cooling nozzle 13 and the fitting 17. In preferred embodiments, the instrument further comprises the solenoid flow controller 15. As illustrated in FIG. 3, the processor 33 controls the flow solenoid 15 to moderate the flow of the fluid, typically air, from the fluid source 35 to the cavity 10. Thus, the flow solenoid 15 is in signal communication with the processor 33, which is also in signal communication with the temperature detector 32. In this manner, the flow solenoid 15 moderates the flow of fluid from the fluid source 35 to the cavity 10 in response to signals from the processor 33. In turn, the signals from the processor 33 to the flow solenoid 15 are based on the data 34 received from the temperature detector 32 and forwarded to the processor 33. The processor can be programmed or used in any appropriate manner, and FIG. 3 illustrates the use of a manual input 36 such as a keyboard or keypad as noted above.

Figure 4:
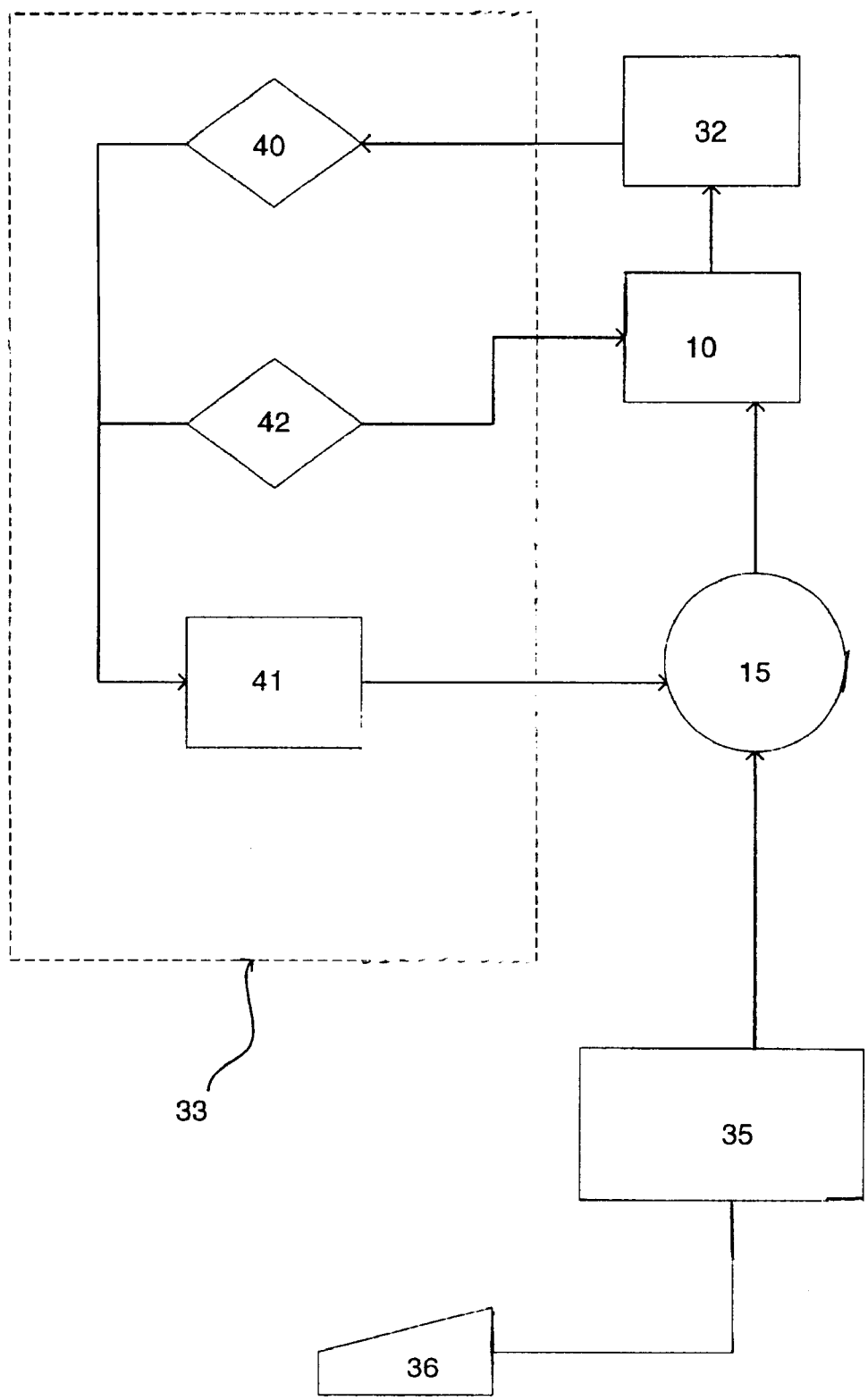
FIG. 4 is a schematic diagram of the operation of a processor in accordance with the present invention.

FIG. 4 is another schematic diagram that shows the logic sequence of the processor 33. FIG. 4 again illustrates the cavity 10, the source of fluid (typically compressed air) 35 the flow solenoid 15 between the fluid source 35 and the cavity 10, and the temperature detector 32. The processor 33 is indicated by the dashed rectangle and includes two decision points, a process capability, and the input device 36. The first decision point is designated at 40 in which the processor evaluates whether the temperature measured by the detector 32 is at the desired set or control point. If the temperature is at the control point, no action is taken. If the temperature is not at the control point, the processor uses the cooling algorithm 41 to control the flow solenoid 15 to moderate the flow of air from the source 35 through the solenoid 15 to the cavity 10. In a similar manner, the processor has the capability of evaluating whether the power is at the desired level as indicated by the decision parallelogram 42.

In this manner, the invention provides the capability to enter a temperature setpoint into the processor, then apply power to the reactants. When the reactants reach the setpoint temperature, the processor can instruct the cooling to begin by controlling the flow solenoid 15. As set forth herein, this permits a greater amount of microwave power to be applied to the reaction because temperature control is carried out in a manner other than reducing the applied power or extending the off portion of the duty cycle. When the reaction is complete (which can also be a pre-set reaction time), the processor can instruct the cooling to continue until the vessel and its contents reach a desired lower temperature, typically a temperature at or near room temperature.

The nature and instructions required to provide such information to a processor of this type are generally well understood in this and other arts and can be practiced by those of ordinary skill in this art without undue experimentation.

As set forth earlier, control systems of this type are generally well understood and can be selected and practiced by those of ordinary skill in this and other arts without undue experimentation. Reasonable discussions of control systems of various types is set forth in Dorf, The Electrical Engineering Handbook, 20th Ed., CRC Press (1997).

Examples Exemplary microwave reactions were carried out using a CEM DISCOVER ™ System single-mode microwave instrument from CEM Corporation, Matthews, N.C. All reactions were performed in specially designed Pyrex pressure tubes equipped with a stir bar and were sealed with a Teflon/silicon septum. All gas chromatograms (GC) and mass spectra (MS) were obtained using a PerkinEimer AutoSystem XL GC/TurboMass MS system. 2-Chloropyridine, 1-methylphenylzinc iodide, furan, and diethylacetylene dicarboxylate were all purchased from Aldrich and were used as received. The organozinc iodide reagent came as a 0.5 M solution in THF in a Sure-Seal bottle. $Pd(P(t-Bu)_3)_2$ was purchased from Strem Chemicals and was used as received.

Figure 5:
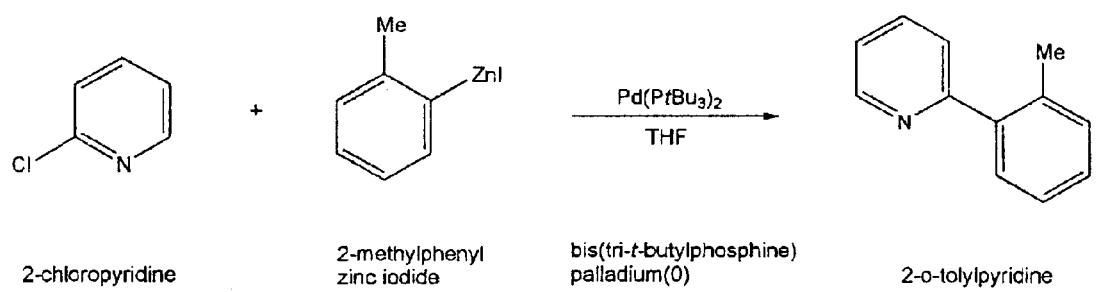
FIG. 5 is the reaction scheme for an exemplary Negishi reaction carried out using the method of the present invention.

Negishi Reaction: Preparation of 2-o-Tolylpyridine. 2-Chloropyridine (100 mg, 0.88 mmol), $Pd(P(t-Bu)_3)_2$ (23 mg, 0.044 mmol), and 1-methylphenylzinc iodide (2.7 mL, 1.3 mmol) were mixed together in a reaction tube. The tube was sealed and the contents were irradiated for 10 min (not including a 1 min ramp time) at 50 W of power and 180° C. In one reaction, simultaneous cooling was administered. The power was increased slowly to 75 W in 5-watt increments and the bulk temperature remained around 150° C. The crude mixture was immediately purified by column chromatography (10:1 hexanes/EtOAc), which yielded a pale yellow liquid. This was analyzed by GC/MS. The MS of this compound was in agreement with the spectrum in the NIST MS library. This compound has been previously prepared and spectroscopically characterized; e.g. Dai, C.; Fu, *G. C. J. Am. Chem. Soc.* 2001, 123, pp. 2719–24. FIG. 5 illustrates the reaction scheme.

Figure 6:
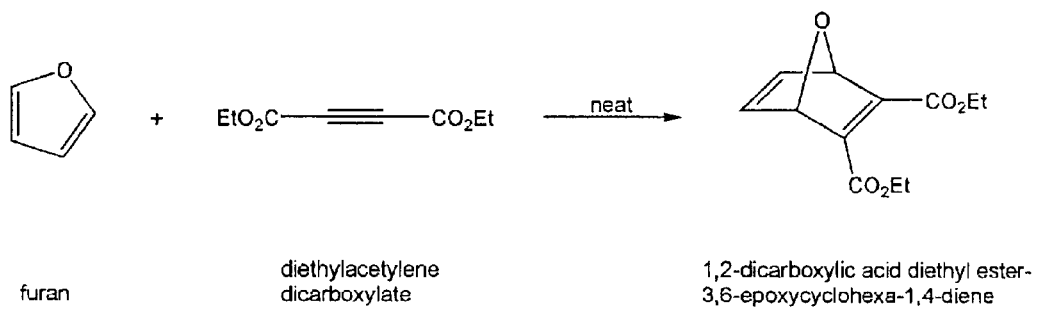
FIG. 6 is the reaction scheme for an exemplary Diels-Alder reaction carried out using the method of the present invention.

Diels-Alder Reaction: Preparation of 1,2-dicarboxylic acid diethyl ester-3,6-epoxycyclohexa-1,4-diene. Furan (100 mg, 0.11 mL, 1.5 mmol) and diethylacetylene dicarboxylate (250 mg, 0.24 mL, 1.5 mmol) were mixed together in a reaction tube. The reaction was performed neat, and with no solvent present. The tube was sealed and the contents were irradiated for 5 min (not including a 5 min ramp time) at 100 W of power and 200° C. In one reaction, simultaneous cooling was administered. The power was increased slowly to 250 W in 10-watt increments and the bulk temperature remained around 120° C. The crude mixture was a dark red oil in the cooled reaction while it was a dark brown tarry substance in the reaction that was not cooled. Both were analyzed by GC/MS. The MS of this compound was in agreement with the spectrum in the NIST MS library. FIG. 6 illustrates this reaction scheme.

FIGS. 7 through 16 represent experimental confirmation of the success of the method of the invention in comparison to more conventional microwave techniques. The figures are either gas chromatograph fraction plots or mass spectra of particular compounds. The theory and operation of gas chromatography and mass spectrometry are well understood in the art, can be practiced by those of ordinary skill in this art, and will not be otherwise discussed in detail herein other than to illustrate the present invention.

Figure 7:
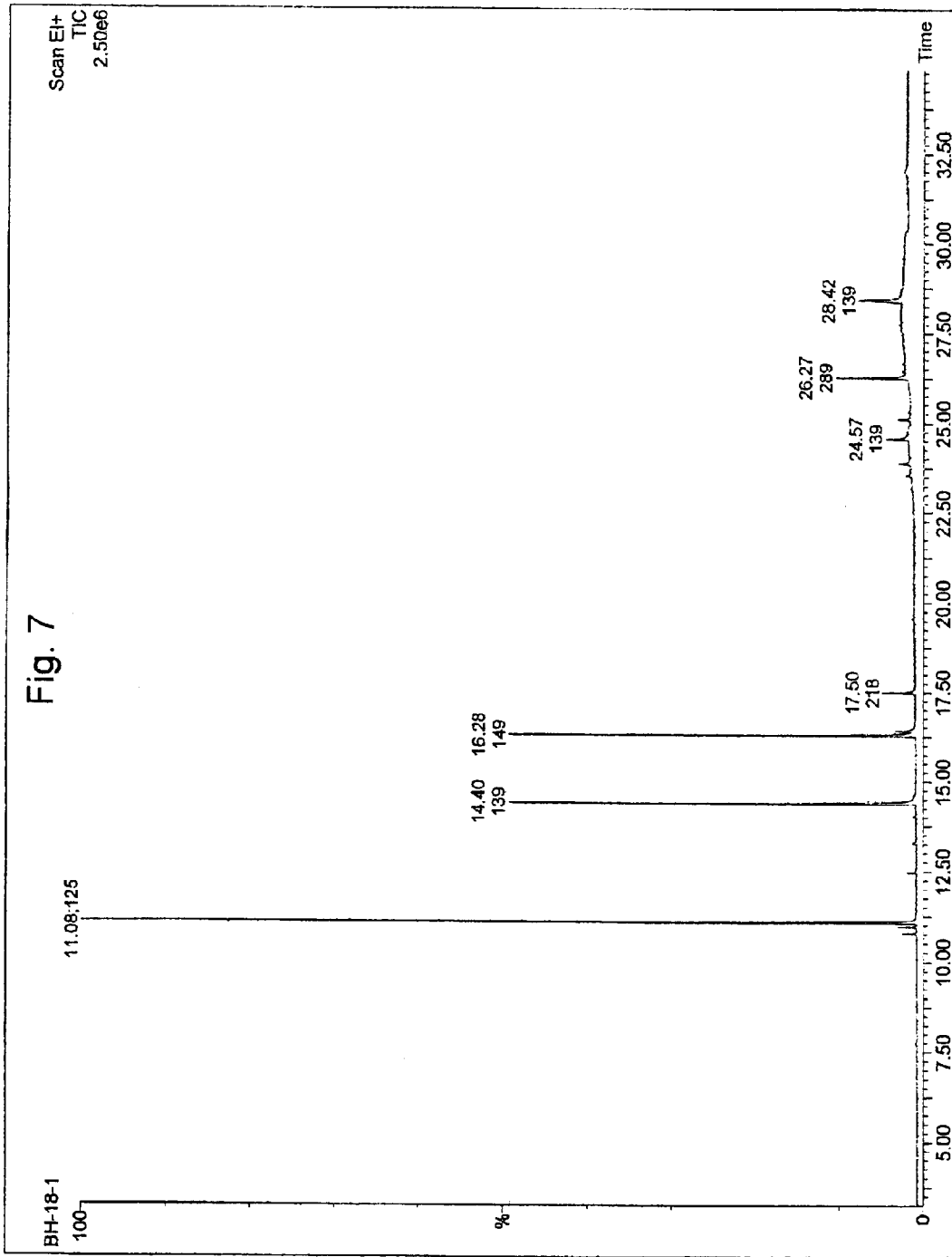
FIG. 7 is a gas chromatogram of a Diels-Alder reaction carried out conventionally between furan and diethylacetylene dicarboxylate to form the bridged cyclohexadiene.

FIG. 7 is the gas chromatograph of the compounds present after carrying out the above-described Diels-Alder reaction under conventional microwave heating (i.e., without the cooling step of the present invention). In the Diels-Alder reaction represented by FIG. 7, the temperature reached as high as 200° C. (heat being a generally expected byproduct of the Diels-Alder reaction) and thus the microwave power applied was limited to 100 watts.

In FIG. 7, the abscissa (x-axis) represents time and thus the individual peaks demonstrate the time at which each fraction exited the column. The ordinate (y-axis) is an arbitrary measure for which 100% represents the largest fraction collected from the column in that particular sample run. Each of the peaks is labeled with two numbers; e.g. 11.08 and 125 for the largest peak in FIG. 7. The first number (11.08) is the retention time for the particular fraction; i.e., the time in minutes after injection at which the fraction exited the column. The second number (125) is obtained from the mass spectra that is carried out of each fraction as it exits the chromatography column and represents the molecular weight of the largest fragment that the mass spectrometer detects from that particular fraction. In FIG. 7, the peak at 11.08 minutes represents the starting material, and the peak at 16.28 minutes represents the desired product, 1,2-dicarboxylic acid diethyl ester-3,6-epoxycyclohexa-1,4-diene. The mass spectra confirms the identity of the compound of the corresponding peak and specifically confirms that the peak at 16.28 minutes is the desired product. Accordingly, all of the remaining peaks represent unreacted starting materials or undesired byproducts. In particular, it will be noted that the byproduct fraction that exits the column at 14.40 minutes (a disubstituted furan in which the substitution groups are ethyl ester) is present in an amount slightly greater than the amount of the desired products (as confirmed by the integrations discussed with respect to FIG. 11). Thus, FIG. 7 shows that when the Diels-Alder reaction between these compounds is carried out under microwave radiation but without cooling, the results include a large amount of unreacted starting material, a large amount of byproduct, and a relatively small, at least as compared to the starting materials, yield of product.

Figure 8:
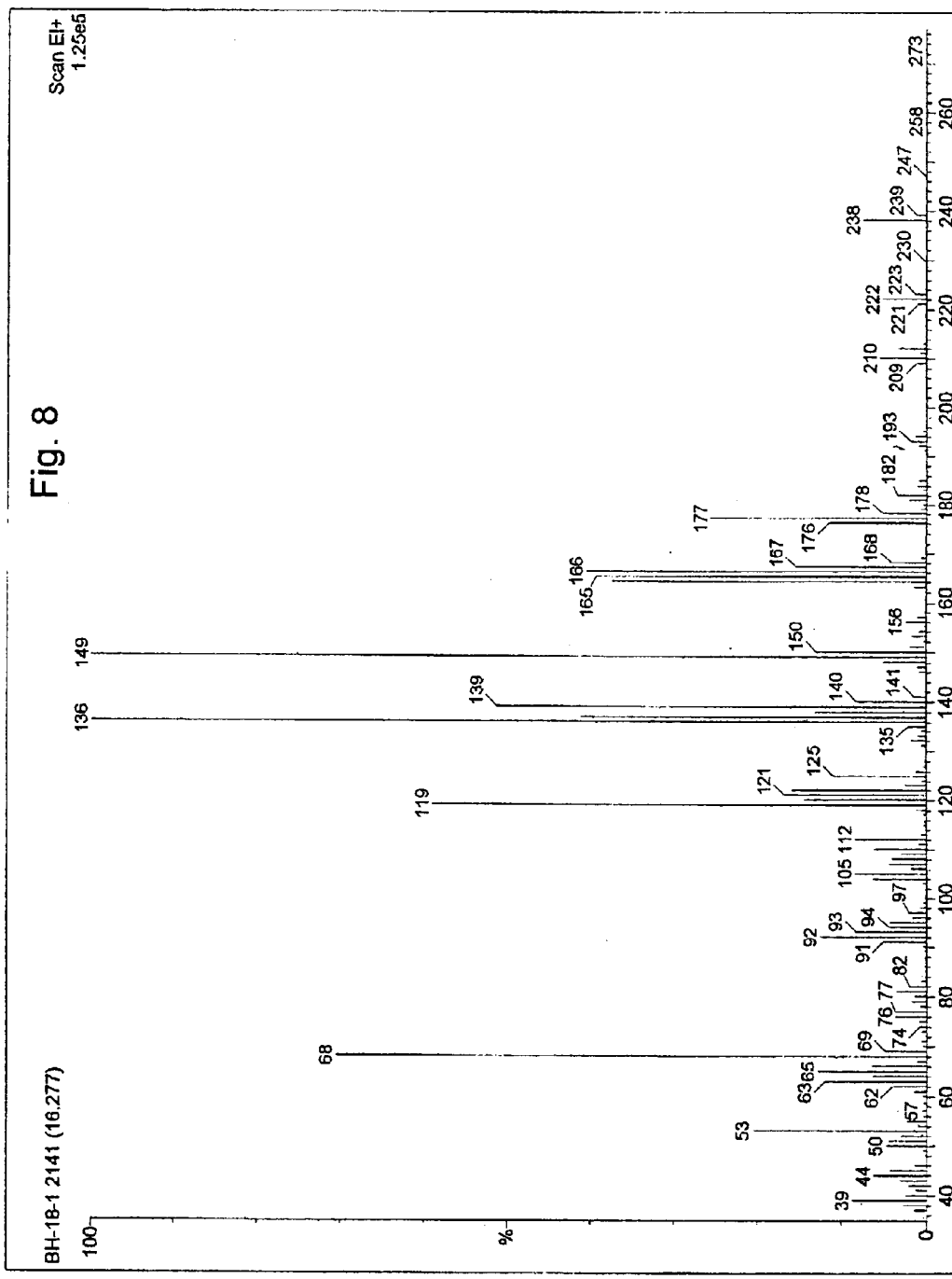
FIG. 8 is the mass spectrum of the product peak from FIG. 7.

FIG. 8 is the mass spectrum of the fraction collected at 16.28 minutes as illustrated in FIG. 7.

Figure 9:
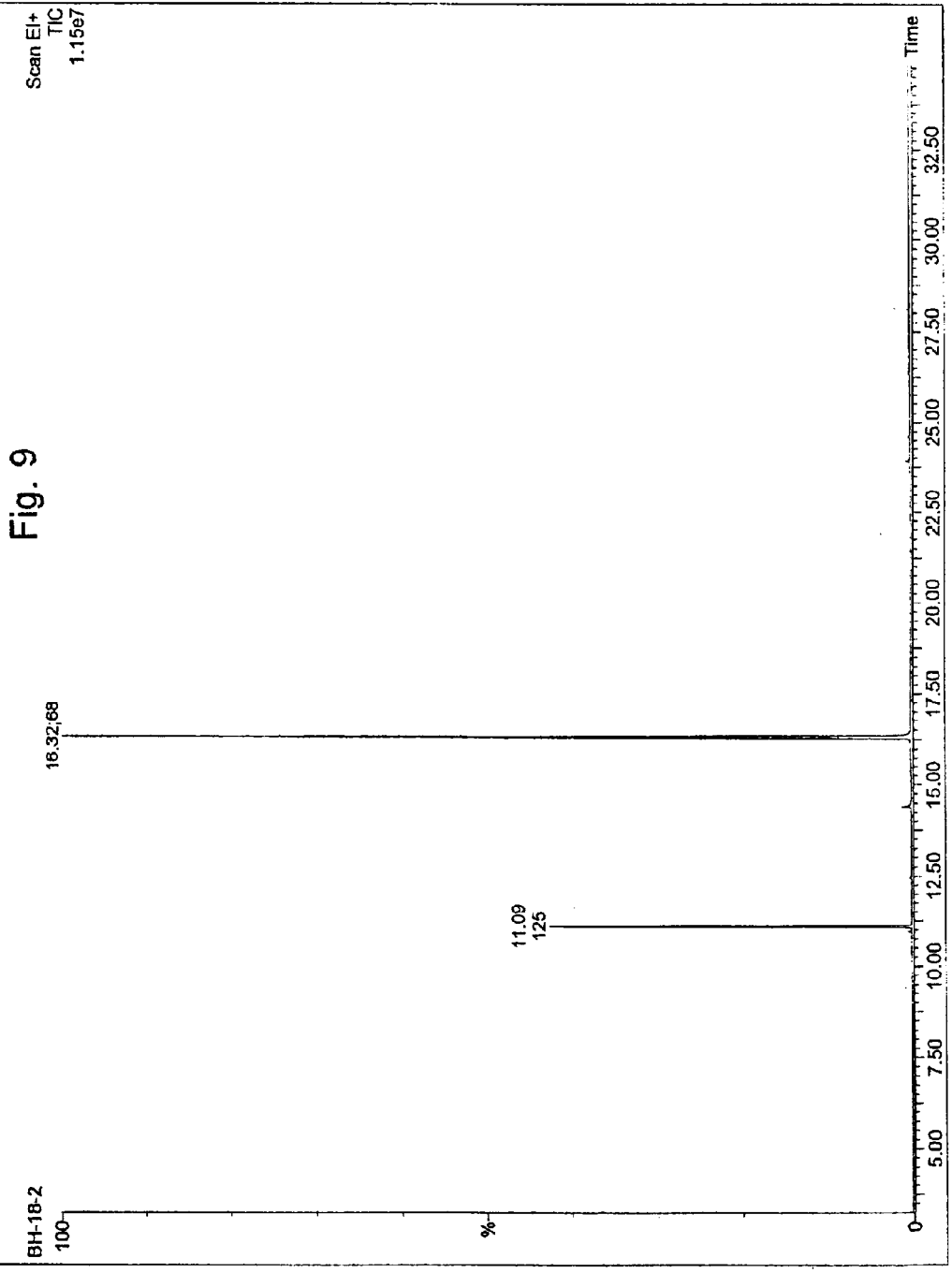
FIG. 9 is the gas chromatogram of the same Diels-Alder reaction, but carried out according to the present invention.

FIG. 9 is the gas chromatograph of the same Diels-Alder reaction represented by the chromatograph of FIG. 7, but with the cooling step of the invention included. As a first point of comparison, when running the Diels-Alder reaction in conjunction with the present invention, the cooling maintained the temperature at between about 100° and 125° C. which allowed the microwave power to be increased to 250 watts.

As another point of comparison, it will be immediately observed that the chromatograph of FIG. 9 is extremely clean in that the dominant fraction obtained is the desired product which exits the column at the same time (within experimental uncertainty) as it did in FIG. 7. It will also be observed that the desired product and its fraction are present in a much greater amount than the starting material illustrating a higher yield from the reaction. Additionally, the lack of other byproduct peaks illustrates that the reaction proceeded more successfully in the desired manner than it did in absence of the invention.

Figure 10:
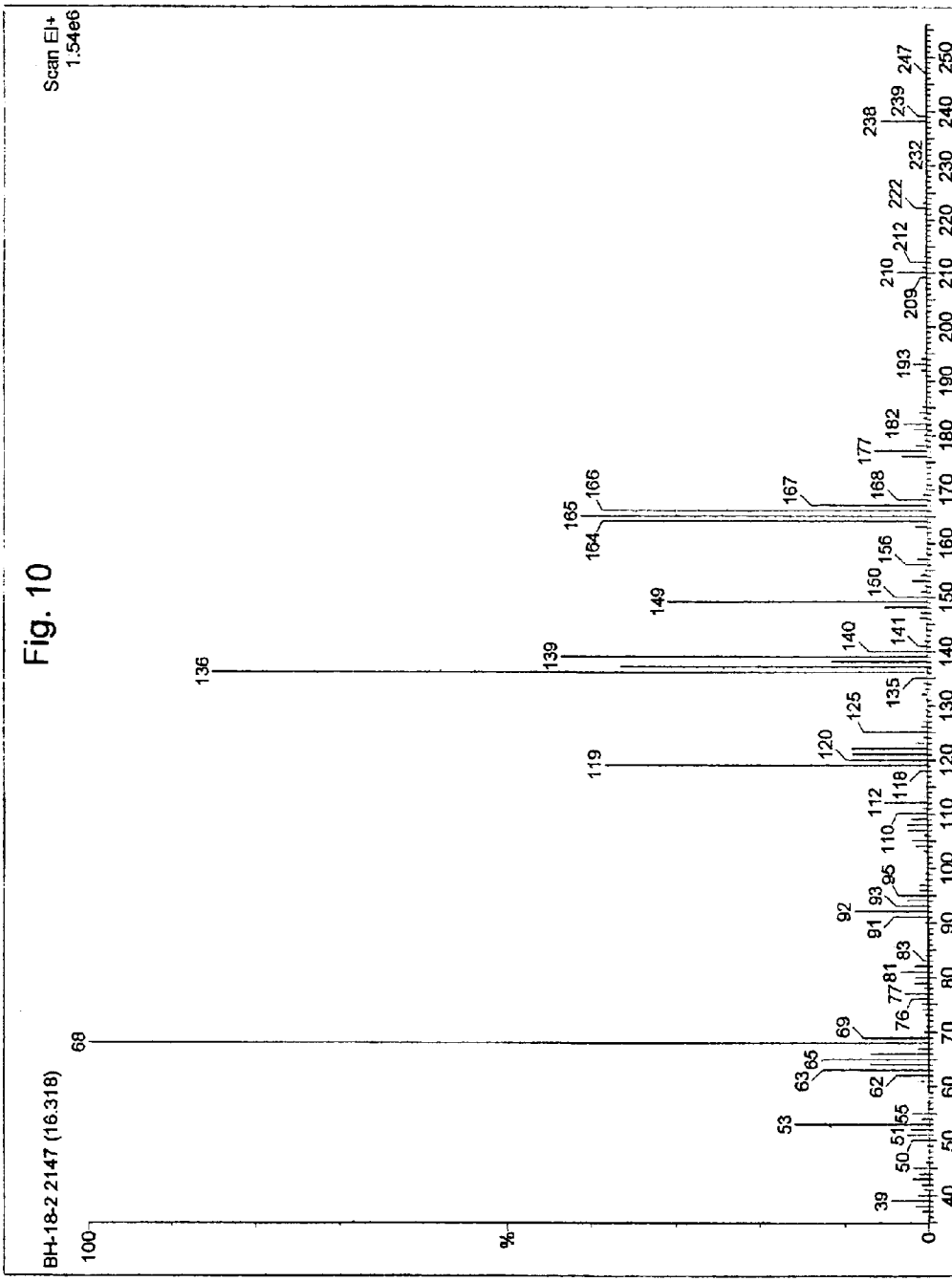
FIG. 10 is the mass spectrum of the product peak of FIG. 9.

FIG. 10 is the mass spectrum of the product peak from FIG. 9 and again confirms that the fraction was the desired product. Although a slightly different number of minutes are plotted in FIG. 10 as compared to FIG. 8, it will be immediately observed that the fragment peaks fall at the same positions (molecular weights) and thus confirm the identity of the desired compound in each case.

Figure 11:
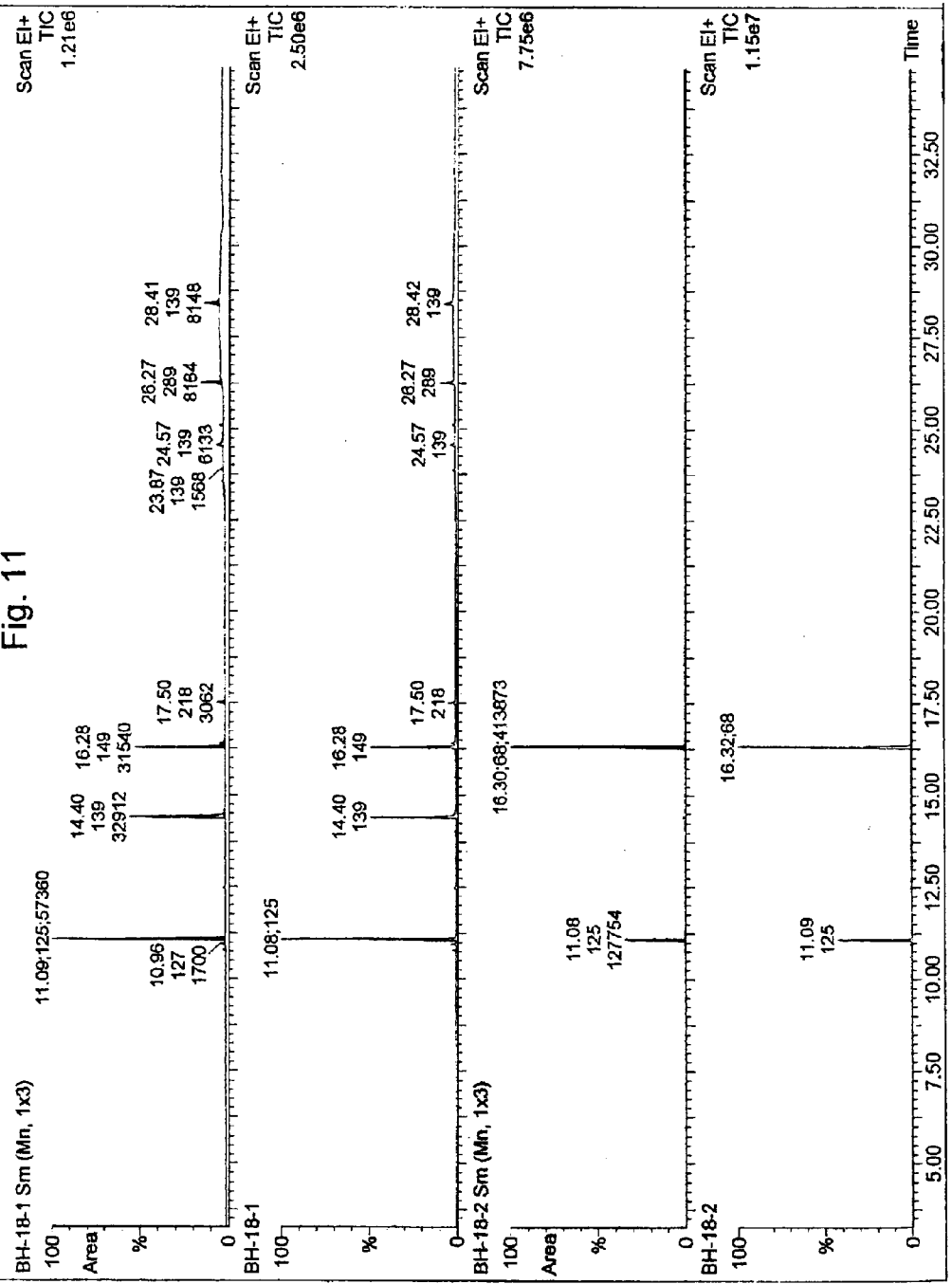
FIG. 11 is another version of the gas chromatogram illustrated in FIGS. 7 and 9, but with the area under the peaks integrated to calculate yields.

FIG. 11 is another set of the gas chromatographs of FIGS. 7 and 9, but with each chromatograph reproduced twice, once with the area under the peak integrated. Accordingly, FIG. 11A represents the Diels-Alder reaction carried out conventionally, and showing the area integrated under the peaks. FIG. 11B is identical to FIG. 11A but without the integration.

In the same manner, FIG. 11C is the same gas chromatograph as FIG. 9 with the peaks integrated, and FIG. 11D is the same as FIG. 11C but without the integration of the peaks.

In FIGS. 11A and 11C, the peaks are identified by three numbers. The first two are the same as previously noted; i.e. the retention time of the fraction in the column, and the molecular weight of the dominating fragment in the mass spectrum. The third number is the area under the peak (in arbitrary units). Accordingly, the yield of any product, byproduct, or even of remaining starting material, can be obtained by dividing the area under its peak by the total area under all of the peaks. In this manner, the integration results of FIG. 11A demonstrate that the yield of the desired product (the fraction exiting at 16.28 minutes) using microwave heating without the cooling step of the invention is only 21%. In comparison, however, FIG. 11C shows that the yield of the desired product is 76% using the method of the invention.

Figure 12:
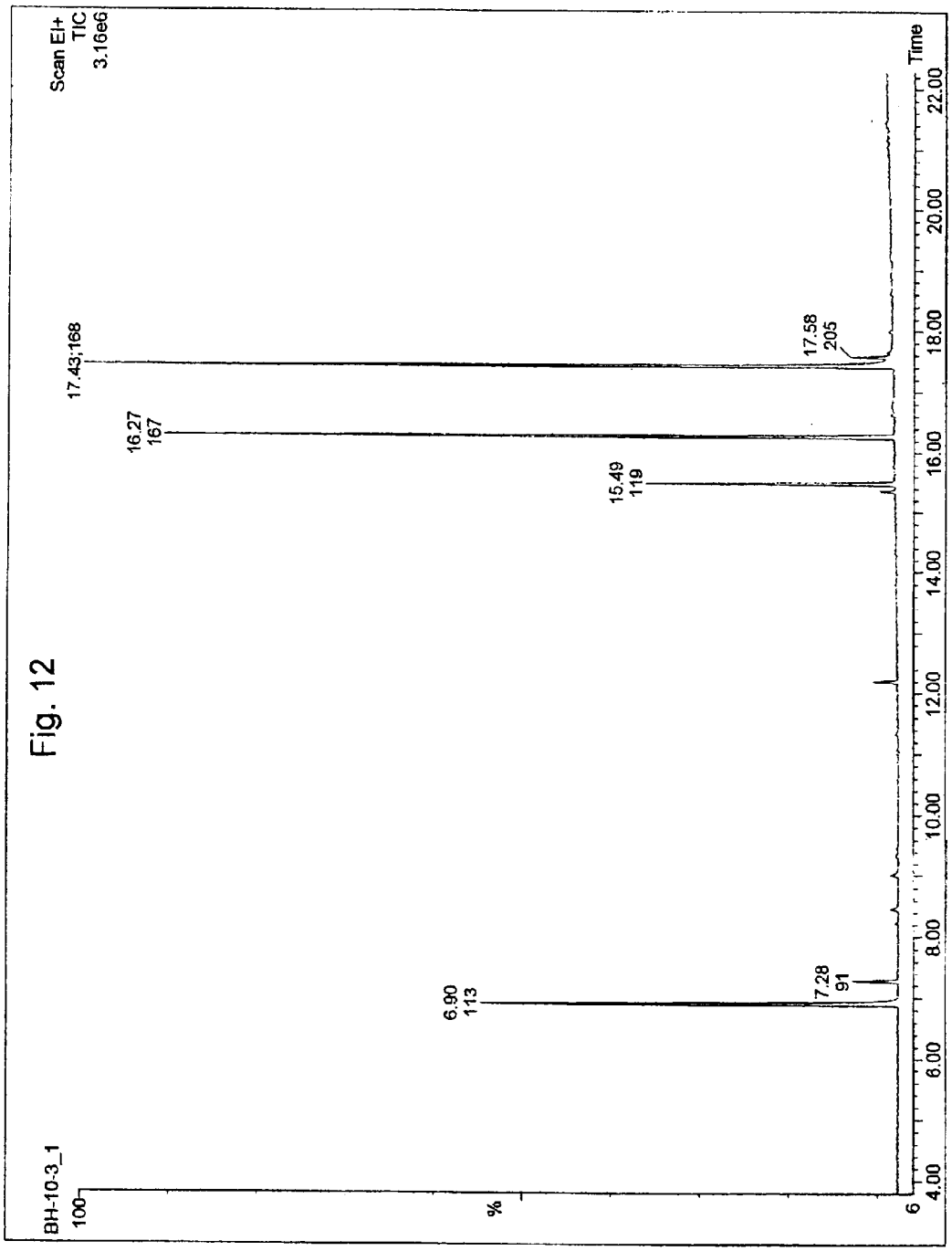
FIG. 12 is the gas chromatogram for a Negishi reaction carried out between 2-chloropyridine and 2-methylphenyl zinc iodide carried out conventionally.

FIG. 12 is the gas chromatograph of the Negishi reaction carried out between 2-chloropyridine and 2-methylphenyl zinc iodide to form 2-o-tolylpyridine. FIG. 12 represents the gas chromatograph when the reaction was carried out using microwave radiation, but not the cooling step. In doing so, the temperature quickly reached as high as 180° C. which required maintaining the microwave power being applied to 50 watts or less. In FIG. 12, the fraction exiting the column at 17.43 minutes (dominant fragment weight 168) represents the desired product. The peak exiting at 6.9 minutes representing the 2-chloropyridine starting material and the peak representing the fraction exiting at 16.27 minutes represents the undesired 2,2'-dimethylbiphenyl byproduct. Several other peaks representing undesired byproducts are likewise present in the chromatograph of FIG. 12. Thus, although FIG. 12 represents a reaction in which the desired product is the largest fraction, its presence is almost entirely matched by the amount of undesired byproducts, along with significant amounts of starting material and other undesired byproducts.

Figure 13:
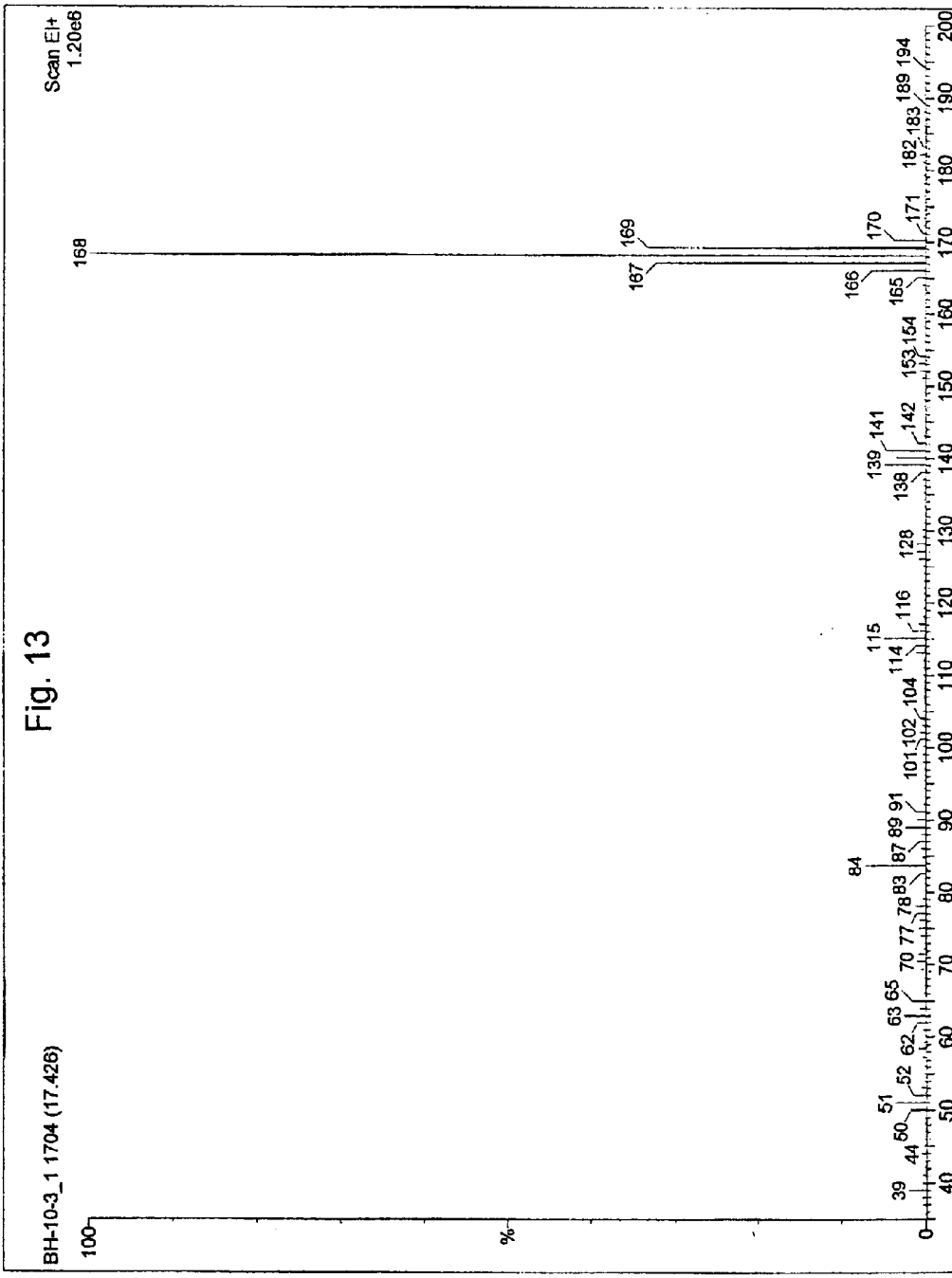
FIG. 13 is the mass spectrum of the product peak of FIG. 12.

FIG. 13 is the mass spectrum of the fraction that exited the column represented by FIG. 12 at 17.43 minutes and confirms the identity of the desired 2-o-tolylpyridine product.

Figure 14:
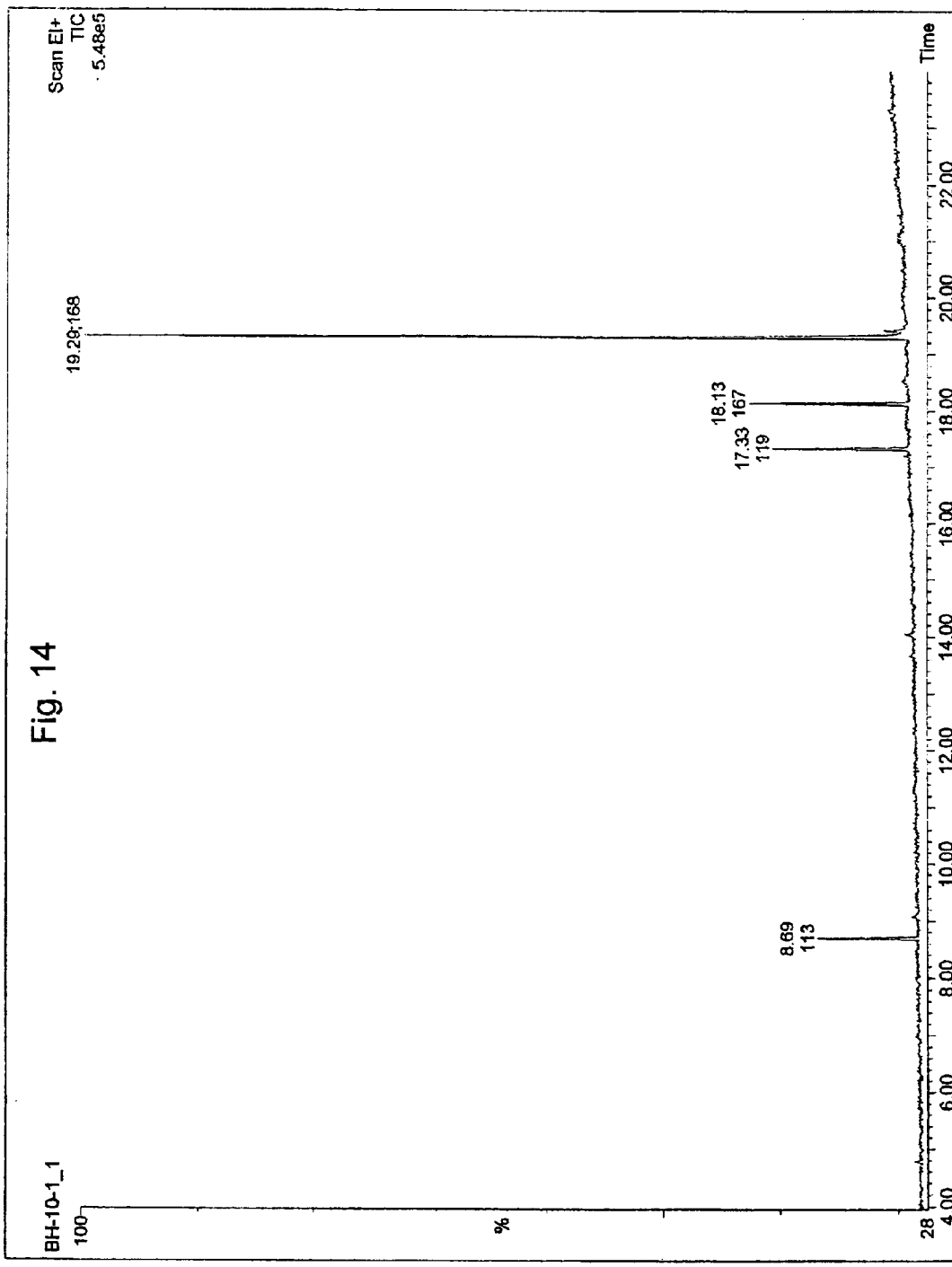
FIG. 14 is the gas chromatogram of the same Negishi reaction carried out using the method of the invention.

FIG. 14 represents the same Negishi reaction using the same starting materials to obtain the same desired product, but carried out using the cooling method of the present invention the cooling enabled the temperature to be maintained at 150° C. or less, which in turn allowed the maximum microwave power to be increased to 75 watts. The products of the reaction represented by FIG. 14 were run through a slightly different gas chromatography column, thus giving retention times that are similar, but not identical, to those in FIG. 12. The molecular weight associated with the dominant fragment in each fraction, however, remained the same and thus the same starting materials and byproducts can be identified. Accordingly, it will be seen that the 2-chloropyridine starting material with its characteristic 9 fraction is present in a much smaller relative amount in FIG. 14 than it was in FIG. 12. Similarly, the undesired 2,2'-dimethylbiphenyl byproduct with the characteristic fragment at 167 is likewise minimal, as are the other byproducts.

Figure 15:
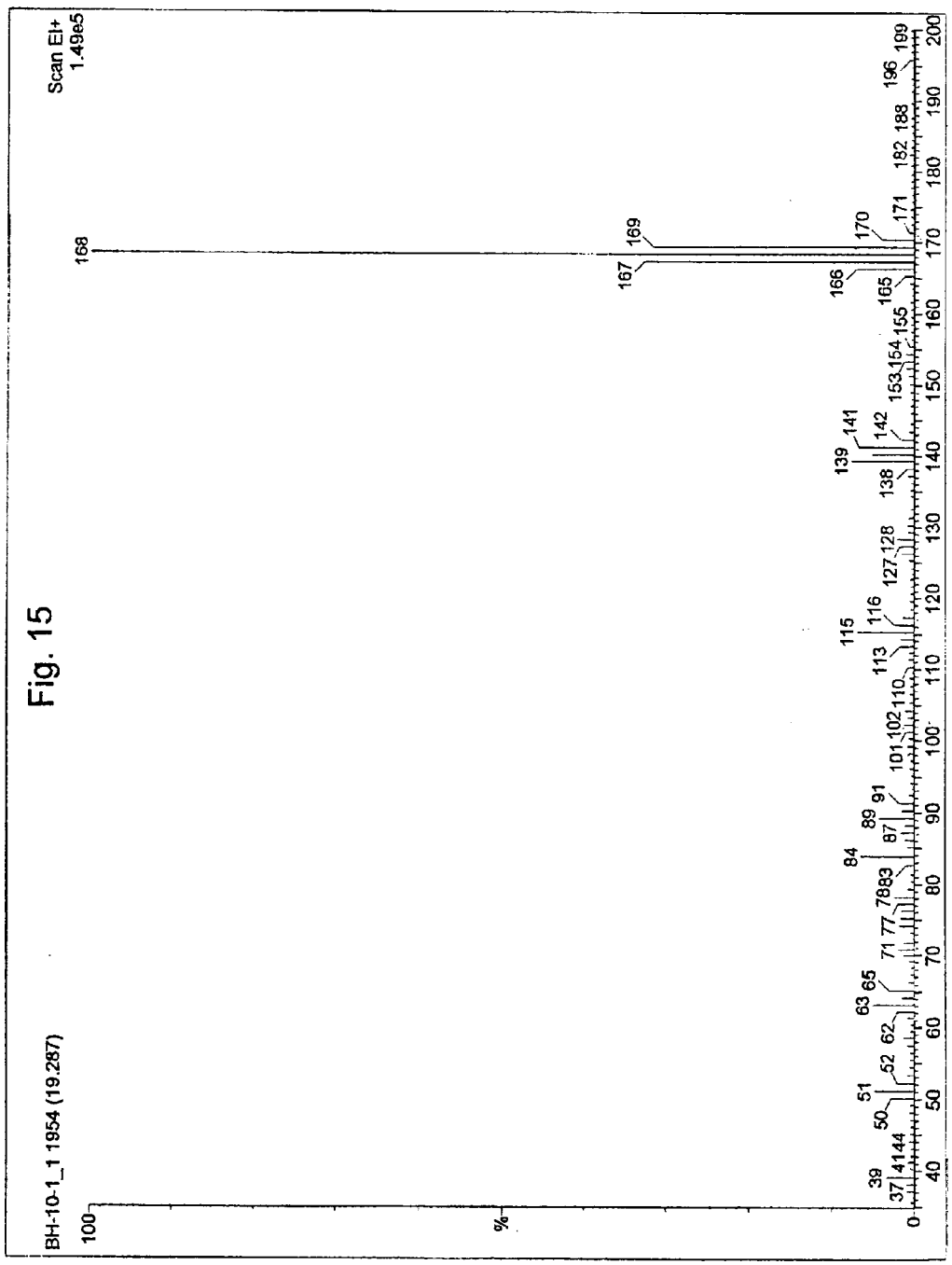
FIG. 15 is the mass spectrum of the product peak/fraction from FIG. 14.

FIG. 15 is the mass spectrum of the fraction that exited the column represented by FIG. 14 at 19.29 minutes, and as in the case of FIG. 13, confirms that the desired product is that fraction.

Figure 16:
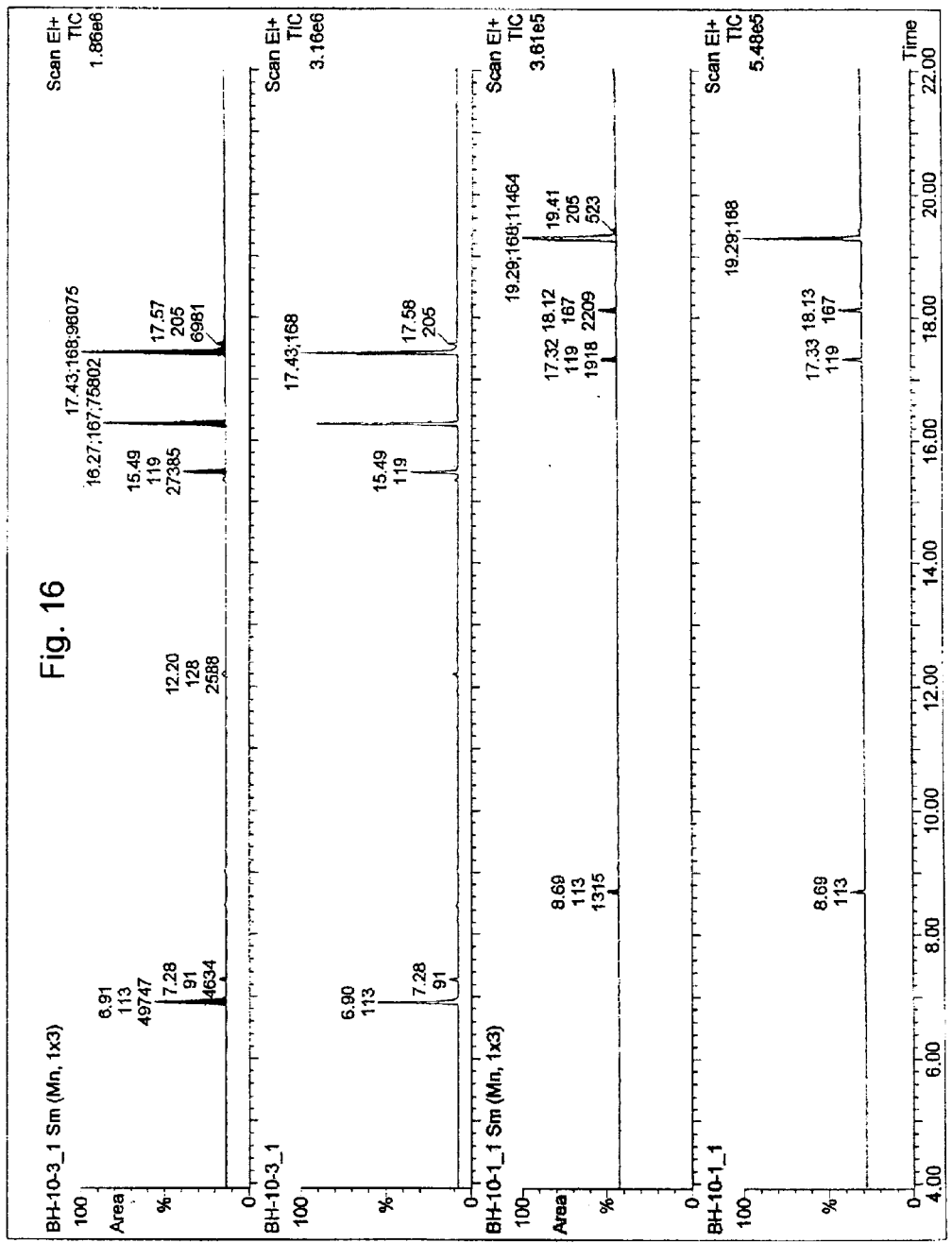
FIG. 16 is another reproduction of the gas chromatogram of FIGS. 12 and 14, with one of each being integrated in order to calculate yields.

FIG. 16 is analogous to FIG. 11 and includes four subparts, A-D, two of which (A and C) include integration of the peaks of the gas chromatograph fractions for the comparative reactions. Accordingly, FIGS. 16A and 16B represent the gas chromatograph results for the Negishi reaction carried out with microwave radiation, but without cooling, and FIGS. 16C and 16D represent the same reaction carried out using the cooling step of the present invention. As with respect to FIG. 11, each peak is characterized by three numbers, the first being the retention time, the second being the molecular weight of the dominant fragment in the fraction as determined by mass spectroscopy, and the third being arbitrary units of area under the peak. Using the same analysis as described with respect to FIG. 11, the yield of the desired product in FIG. 16A (the fraction at 17.43 minutes) using conventional microwave techniques is 36.5 percent. In FIG. 16C, and using the method of the invention, the yield is 66 percent.:

These results can also be summarized in tabular forms

| Reaction | Time (Minutes) | Temperature (Degrees C.) | Power (Watts) | Yield |
|---|---|---|---|---|
| Diels-Alder (Conventional Microwave) | 5 | 200 | 100 | 21 |
| Diels-Alder (Invention) | 5 | 120 | 250 | 76 |
| Negishi (Conventional Microwave) | 10 | 180 | 50 | 36.5 |
| Negishi (Invention) | 10 | 150 | 75 | 66 |

In the drawing's and specification there has been set forth a preferred embodiment of the invention, and although specific terms have been employed, they are used in a generic and descriptive sense only and not for purposes of limitation, the scope of the invention being defined in the claims.

What is claimed is:

1. A method of carrying out microwave assisted chemical reactions, the method comprising:
    placing reactants in a microwave-transparent vessel;
    placing the vessel and its contents into a microwave cavity; and
    applying a continuous single mode of microwave radiation within the cavity and to the vessel and its contents while concurrently externally cooling the vessel.

2. A method according to claim 1 comprising placing the reactants in a pressure-resistant vessel and sealing the vessel prior to the step of applying the microwave radiation.

3. A method according to claim 1 comprising concurrently measuring the temperature of the vessel or its contents while applying the microwave radiation.

4. A method according to claim 1 wherein the step of placing the vessel and its contents into the microwave cavity comprises robotic transfer of the vessel.

5. A method according to claim 1 comprising applying the microwave radiation from a source selected from the group consisting of magnetrons, klystrons and solid state sources.

6. A method according to claim 3 wherein the step of cooling the vessel and its contents comprising directing an air flow over the vessel at a rate sufficient to maintain the vessel and contents at a desired temperature.

7. A method according to claim 6 comprising directing the air flow intermittently.

8. A method according to claim 6 comprising changing the rate of air flow in response to the measured temperature.

9. A method according to claim 6 comprising directing the air flow at a rate of between about 1 and 80 psi.

10. A method according to claim 1 wherein the step of applying continuous microwave radiation comprises applying radiation from a source and driving the source at a frequency of greater than 60 hertz.

11. A method according to claim 1 wherein the step of applying continuous microwave radiation comprises applying radiation from a source and driving the source at a frequency of greater than 600 hertz.

12. A method according to claim 1 wherein the step of applying continuous microwave radiation comprises applying radiation from a source and driving the source at a frequency of greater than 6000 hertz.

13. A method according to claim 1 wherein the step of applying continuous microwave radiation comprises applying radiation from a source and driving the source at a frequency of between about 10,000–250,000 hertz.

14. A method according to claim 1 comprising cooling the vessel continuously.

15. A method according to claim 1 wherein the step of applying a single mode of microwave radiation comprises propagating the microwaves into a cavity that limits the radiation to a single mode.

16. A method of carrying out microwave assisted chemical reactions, the method comprising:
    placing reactants in a microwave-transparent pressure resistant vessel and sealing the vessel;
    placing the sealed vessel and its contents into a microwave cavity;
    applying microwave radiation continuously within the cavity and to the vessel and its contents;
    while monitoring the temperature of the vessel; and
    while concurrently externally cooling the sealed vessel and its contents.

17. A method according to claim 16 wherein the step of placing the vessel and its contents into the microwave cavity comprises robotic transfer of the vessel.

18. A method according to claim 16 comprising applying the microwave radiation from a source selected from the group consisting of magnetrons, klystrons and;solid state sources.

19. A method according to claim 16 wherein the step of cooling the vessel and its contents comprising directing an air flow over the vessel at a rate sufficient to maintain the vessel and contents at a desired temperature.

20. A method according to claim 19 comprising directing the air flow intermittently.

21. A method according to claim 19 comprising changing the rate of air flow in response to the measured temperature.

22. A method according to claim 19 comprising directing the air flow at a rate of between about 1 and 80 psi.

23. A method according to claim 16 wherein the step of applying continuous microwave radiation comprises applying radiation from a source and driving the source at a frequency of greater than 60 hertz.

24. A method according to claim 16 wherein the step of applying continuous microwave radiation comprises applying radiation from a source and driving the source at a frequency of greater than 600 hertz.

25. A method according to claim 16 wherein the step of applying continuous microwave radiation comprises applying radiation from a source and driving the source at a frequency of greater than 6000 hertz.

26. A method according to claim 16 wherein the step of applying continuous microwave radiation comprises applying radiation from a source and driving the source at a frequency of between about 10,000–250,000 hertz.

27. A method according to claim 16 comprising cooling the vessel continuously.

28. A method of carrying out microwave assisted chemical reactions, the method comprising:
    placing reactants in a microwave-transparent vessel;
    placing the vessel and its contents into a microwave cavity;
    monitoring the temperature of the vessel or its contents; and
    applying a continuous single mode of microwave radiation within the cavity and to the vessel and its contents until the temperature reaches a desired setpoint; and
    concurrently externally cooling the vessel and its contents while applying the continuous microwave radiation to maintain the temperature substantially at the setpoint.

29. A method according to claim 28 comprising placing the reactants in a pressure-resistant vessel and sealing the vessel.

30. A method according to claim 28 comprising continuously monitoring the temperature.

31. A method according to claim 28 comprising initiating the cooling step when the monitored temperature reaches a designated setpoint.

32. A method according to claim 28 wherein:
    the cooling step comprises cooling the vessel with a fluid from a fluid source; and
    the step of applying the microwave radiation comprises maximizing the microwave power at the capacity of the cooling source while maintaining the temperature substantially at the set point.

33. A method according to claim 28 comprising changing the desired setpoint and carrying out the steps of applying microwave radiation and external cooling to reach and maintain the temperature at the new setpoint.

34. A method according to claim 28 wherein the step of placing the vessel and its contents into the microwave cavity comprises robotic transfer of the vessel.

35. A method according to claim 28 comprising applying the microwave radiation from a source selected from the group consisting of magnetrons, klystrons and solid state sources.

36. A method according to claim 28 wherein the step of cooling the vessel and its contents comprising directing an air flow over the vessel at a rate sufficient to maintain the vessel and contents at a desired temperature.

37. A method according to claim 36 comprising directing the air flow intermittently.

38. A method according to claim 36 comprising changing the rate of air flow in response to the measured temperature.

39. A method according to claim 36 comprising directing the air flow at a rate of between about 1 and 80 psi.

40. A method according to claim 28 wherein the step of applying continuous microwave radiation comprises applying radiation from a source and driving the source at a frequency of greater than 60 hertz.

41. A method according to claim 28 wherein the step of applying continuous microwave radiation comprises applying radiation from a source and driving the source at a frequency of greater than 600 hertz.

42. A method according to claim 28 wherein the step of applying continuous microwave radiation comprises applying radiation from a source and driving the source at a frequency of greater than 6000 hertz.

43. A method according to claim 28 wherein the step of applying continuous microwave radiation comprises applying radiation from a source and driving the source at a frequency of between about 10,000–250,000 hertz.

44. An instrument for carrying out microwave assisted chemical reactions, said instrument comprising:
- a microwave cavity;
- a microwave-transparent vessel in said cavity;
- a detector for monitoring the temperature of said vessel or its contents in said cavity;
- means for applying a continuous single mode of microwave radiation within said cavity and to said vessel and its contents until the temperature reaches a desired setpoint as measured by said detector; and
- means for concurrently externally cooling said vessel and its contents while applying the continuous microwave radiation; and
- means for maintaining the temperature substantially at the setpoint while applying the microwave radiation.

45. An instrument according to claim 44 wherein said microwave applying means comprises a source and a waveguide in communication with said source and said cavity.

46. An instrument according to claim 44 wherein said temperature maintaining means comprises a processor in signal communication with said detector.

47. An instrument according to claim 46 wherein said cooling means comprises a source of cooling fluid and a fluid communication path from said source to said cavity.

48. An instrument according to claim 47 wherein said temperature maintaining means further comprises a flow controller in signal communication with said processor and in fluid communication with said fluid source and said cavity for moderating the flow of fluid from said source to said cavity in response to signals from said processor.

49. An instrument according to claim 48 wherein said processor controls said flow controller in response to temperature data from said detector.

50. An instrument according to claim 48 wherein said flow controller comprises a solenoid valve and said fluid communication path comprises a tube between said solenoid and said cavity.

51. An instrument according to claim 44 wherein said detector is an infrared temperature detector.

52. An instrument according to claim 44 comprising an input device for providing said processor with data selected from the group consisting of microwave power levels, durations of microwave application and setpoint temperatures.

* * * * *